United States Patent [19]
Rose et al.

[11] Patent Number: 5,965,086
[45] Date of Patent: Oct. 12, 1999

[54] METHOD FOR MAKING STERILE CONNECTIONS BETWEEN FLUID CONDUIT TUBES

[75] Inventors: Sam Rose, Emeryville; Glenn C. Buchanan, Belmont, both of Calif.

[73] Assignee: Baxter Healthcare Corporation, Irvine, Calif.

[21] Appl. No.: 08/009,381

[22] Filed: Jan. 27, 1993

Related U.S. Application Data

[63] Continuation of application No. 07/730,586, Jul. 15, 1991, abandoned, which is a continuation of application No. 07/348,280, May 5, 1989, abandoned.

[51] Int. Cl.⁶ ...................................................... A61L 2/08
[52] U.S. Cl. ........................... 422/22; 422/1; 422/186.29; 604/405
[58] Field of Search .................... 422/186.29, 1, 422/22; 525/479; 604/405

[56] References Cited

U.S. PATENT DOCUMENTS

| | | | |
|---|---|---|---|
| 3,961,150 | 6/1976 | Lewis et al. | 422/22 X |
| 3,968,195 | 7/1976 | Bishop | 264/154 |
| 3,986,508 | 10/1976 | Barrington | 128/214.2 |
| 4,004,586 | 1/1977 | Christensen et al. | 128/214 D |
| 4,030,494 | 6/1977 | Tenczar | 604/905 X |
| 4,130,599 | 12/1978 | Merrill et al. | 525/477 |
| 4,242,310 | 12/1980 | Greff et al. | 422/300 |
| 4,251,310 | 2/1981 | Goldhaber et al. | 156/273 |
| 4,340,097 | 7/1982 | Ammann et al. | 141/98 |
| 4,369,779 | 1/1983 | Spencer | 128/213 |
| 4,412,835 | 11/1983 | Spencer | 604/29 |
| 4,439,193 | 3/1984 | Larkin | 604/411 |
| 4,443,215 | 4/1984 | Smith | 604/905 X |
| 4,458,153 | 7/1984 | Wesley | 422/22 X |
| 4,473,369 | 9/1984 | Lueders et al. | 604/244 |
| 4,475,900 | 10/1984 | Popovich et al. | 604/905 X |
| 4,507,119 | 3/1985 | Spencer | 604/280 |
| 4,516,971 | 5/1985 | Spencer | 604/280 |
| 4,610,670 | 9/1986 | Spencer | 604/29 |
| 4,619,642 | 10/1986 | Spencer | 604/29 |
| 4,668,217 | 5/1987 | Isono | 604/49 |
| 4,782,231 | 11/1988 | Svoboda et al. | 422/159 X |

FOREIGN PATENT DOCUMENTS

| | | |
|---|---|---|
| WO 8202528 | 8/1982 | WIPO . |
| WO 8302060 | 6/1983 | WIPO . |
| WO 8402321 | 6/1984 | WIPO . |

OTHER PUBLICATIONS

Webster's Ninth New Collegiate Dictionary, 1986, p. 1224.
Hanley's Condensed Chemical Dictionary, 11th Ed, Van Nostrand Reinhold Co., New York, 1987, pp. 1147, 1039.
"Product Literature", Fenwal Sterile Connection System.
"Product Literature", duPont Sterile Connection Technology.

*Primary Examiner*—Timothy McMahon
*Attorney, Agent, or Firm*—St. Onge Steward Johnston & Reens LLC

[57] ABSTRACT

Sterile interconnection between disassociated segments of thermostable, compressible fluid conduit tubing is achieved by arranging within the bore of the free end of each segment a conductive hollow metal tube so as to establish a connected fluid flow path from one segment to the other, through the metal tube, and then sterilizing the connection by induction heating.

3 Claims, 4 Drawing Sheets

METHOD FOR MAKING STERILE CONNECTIONS BETWEEN FLUID CONDUIT TUBES

This is a continuation of application Ser. No. 07/730,586 filed on Jul. 15, 1991 now abandoned which is a continuation of Ser. No. 07/348,280 filed May 5, 1989 now abandoned.

BACKGROUND OF THE INVENTION

The present invention relates to the making of sterile connections between fluid conduit tubes and, more particularly, to a method and apparatus for joining in a sterile manner two disassociated fluid conduit tubes so as to enable fluid communication of sterile fluids therebetween.

There are many situations in the medical, scientific and biological arts where it is necessary to effectuate in systems the sterile transfer of fluids from one container to another, one apparatus to another, and the like. Generally speaking, the containers, apparatus, fluid conduit tubes and the like can be sterilized en masse for initial use so as to insure a microorganism-free environment, but innumerable situations arise where it is necessary to invade the sterile environment so as, for example, to add additional apparatus, remove samples, or the like. While the so-altered unit or system can perhaps be resterilized in toto before being placed back in use, this is an unsatisfactory approach in terms of time, convenience and economics.

Exemplary situations where these problems are encountered include supplying of blood or other essential fluids to a patient where it may be necessary to invade an initially sterile system so as to remove a depleted container of fluid and bring on stream a new supply of fluid. In such fields, the art has devoted considerable attention to the provision of means for effecting the sterile connections needed for adding or deleting components in the system. Some of the many patents in this area include U.S. Pat. No. 3,986,508 assigned to Abcor, Inc.; U.S. Pat. No. 4,475,900 to Popovich, et al.; U.S. Pat. No. 4,668,217 to Isono; U.S. Pat. Nos. 4,004,586, 4,242,310, 4,340,097, 4,473,369, and PCT Publications WO 84/02324, WO 83/02060 and WO 82/02528, all assigned to Baxter-Travenol Laboratories; and U.S. Pat. Nos. 4,369,779, 4,412,835, 4,443,215, 4,516,971, 4,507,119, 4,610,670 and 4,619,642, all assigned to E. I. duPont de Nemours & Co. In large part, these teachings involve relatively intricate connecting systems, melting of thermoplastic tube ends, and other like techniques.

Although given little attention in the art, another field where provision of sterile connections is of considerable importance is the in vitro culture of animal cells, a field of increasing importance for the production and recovery of cell-secreted proteins for therapeutic and/or diagnostic use. Since the culturing animal cells in such systems are arranged to grow and subdivide and produce product as if they were in an in vivo environment but are without the elaborate immune defense system which normally exists in that in vivo environment, the need for sterile culture conditions is quite apparent. In typical practice, the culture unit and its associated components (e.g., fluid conduit tubes for providing fresh medium and for withdrawing spent medium, oxygenation means, and the like) are provided in pre-sterilized format. However, the occasions are many where this sterile system must be invaded, either to cut in or delete culture medium containers, provide for cell and/or culture fluid analyses, add or delete culture chambers, and the like. Operation in a manner which requires that the system be resterilized in toto for each such invasion adds enormously to the complexity and cost of the culture operation. So too, reliance upon complex sterile connection schemes adds to the cost of operation and may result in yet further costs associated with the personnel required in order to correctly perform the needed operations.

In view of the foregoing, the primary object of the present invention is to provide a method and apparatus for quickly, simply and inexpensively effecting sterile connection between two disassociated fluid conduit tubes, whether they be tubes associated with containers or other apparatus, so that there can be established or reestablished a flow of sterile fluid through the connected tubing.

A more particular object of the invention is to provide a method and apparatus for interrupting a sterile fluid flow path through conduit tubing, e.g., by cutting through the tubing, and then effecting sterile connection between at least one of the resulting tube segments and another tube segment so as to reestablish a sterile flow of fluid through the newly-connected tubes. A still further object in this regard is to provide a method for this purpose which affords significant flexibility to the technician with respect to where along such tubing the interruption and connection can be effected.

SUMMARY OF THE INVENTION

In accordance with the present invention, there is provided a method for forming a sterile connection between two disassociated segments of thermostable fluid conduit tubing, each segment having a free end, comprising arranging respective ends of a hollow conductive metal tube within the bore of each of the fluid conduit tubes at their free ends so as to form a connected fluid flow path from one tubing segment, through said hollow metal tube, to the other tubing segment; and heating at least a portion of the connected flow path, including said hollow metal tube, by means of induction heating, to a temperature sufficient to sterilize the connected flow path.

In accordance with more specific aspects of the invention, the disassociated segments of thermostable tubing are each in fluid communication with a sterile segment of tubing or sterile device. Near the free end of each segment, means are employed to isolate the free end of the tubing from the sterile segment thereof. The so-isolated, non-sterile free end segments are then brought into general alignment and connected by means of a hollow metal tube inserted into the bore of each of the free, non-sterile end segments. Thereafter, at least a portion of the isolated and connected segments, including the metal tube therebetween, is arranged to lie within the field of a primary induction work coil such that, when an alternating current is applied to the work coil, a reverse alternating current is generated in the portion of the conductive metal tube lying within the field of the work coil, causing the conductive metal tube to be heated to a temperature sufficient to kill bacteria, microorganisms and other contaminants within the metal tube bore as well as within the entirety of the bores of the isolated, connected tubing segments. Thereafter, the means by which the tubing segments were isolated from their sterile segments are removed, establishing a sterile fluid communication between such segments, through the sterilized connection. In a preferred embodiment, means are employed for forming a compressive seal between the isolated tubing segments and the portion of the metal tube arranged in their bores before removing the isolating means.

The method of the present invention can be used in any environment where it is necessary to form a sterile connection between two disassociated non-sterile tubing segments, whether to add or delete sterile tubing, supply or collection containers, other devices or the like, provided that the tubing segments are made of materials which are thermostable under the sterilizing induction heating conditions, compressible so as to permit isolation of non-sterile segments from sterile segments thereon, and recoverable after compression so as to reestablish fluid flow therein.

In the apparatus of the present invention, a primary induction work coil is provided, in a configuration which provides an elongate channel in which the tubing segments, connected by a hollow conductive metal tube, can be arranged so as to lie within the field of the work coil to effect inductive heating of the conductive metal tube.

DETAILED DESCRIPTION OF THE INVENTION

Figure 1:
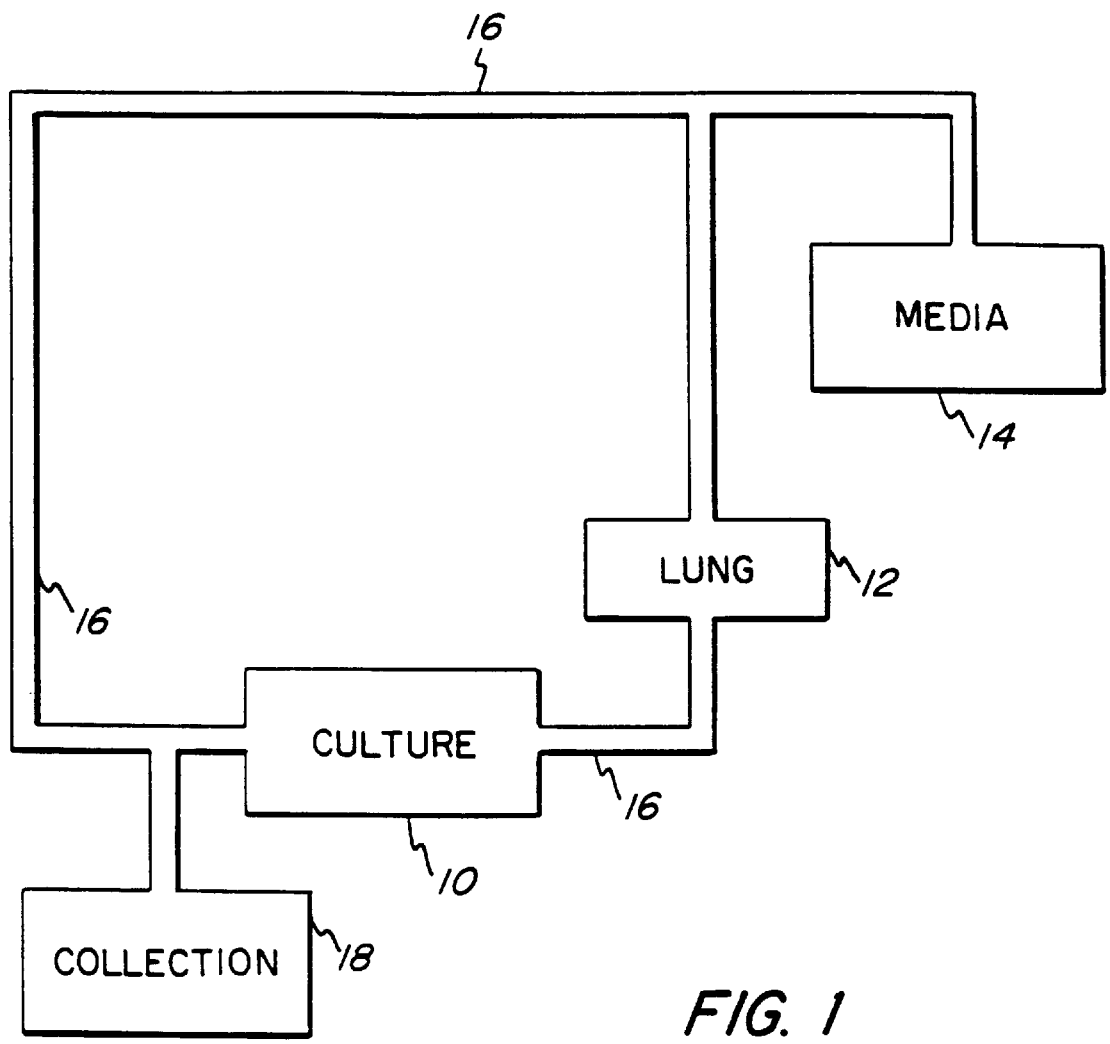
FIG. 1 is a schematic illustration of an animal cell culture system utilizing silicone rubber tubing for interconnecting the components of the system and for flowing fresh culture medium and removing and/or recycling a flow of spent culture medium.

In discussion of detailed aspects of the invention, reference is had to its use in making sterile connections in the operation of a typical animal cell culture unit, as shown schematically in FIG. 1, simply for purposes of ease of description and illustration. As will be apparent, however, the environment in which the invention is employed, be it a culture system, a blood delivery system, an ambulatory peritoneal dialysis system, or the like, is not material to the fundamental operation of the invention.

As noted, a typical animal cell culture system is shown schematically in FIG. 1, consisting of a culture unit 10, means 12 for providing oxygen and/or $CO_2$ to fresh culture medium, a source of fresh culture medium 14, and silicone tubing 16 through which culture fluid is fed to the culture unit and spent medium is withdrawn from the culture unit. Also shown is a product collection container 18 into which at least a portion of the spent medium exiting from the culture unit, which contains protein products secreted by the culturing cells, is arranged to flow.

At the start of the culture process, the system components and fluids are in sterile connection, e.g., as a consequence of sterilization of the entire assembled system and utilization of sterile culture medium. As will be apparent, and as discussed hereinafter, the present invention can itself be employed in arranging for sterile assembly and interconnection of the various components of the culture system, i.e., wherein pre-sterilized components can be assembled in a sterile manner rather than sterilizing the entire assembled system en masse. For present discussion, however, the description relates to an already sterile system (however obtained) which must be invaded for some reason.

In the culture system shown, for example, it may be necessary at some point in time to remove from the system a filled product collection container 18 and replace it with a new, empty container. According to the invention, this operation is accomplished in the following manner, as illustrated in further detail in FIGS. 2A–2E.

Figure 2A:
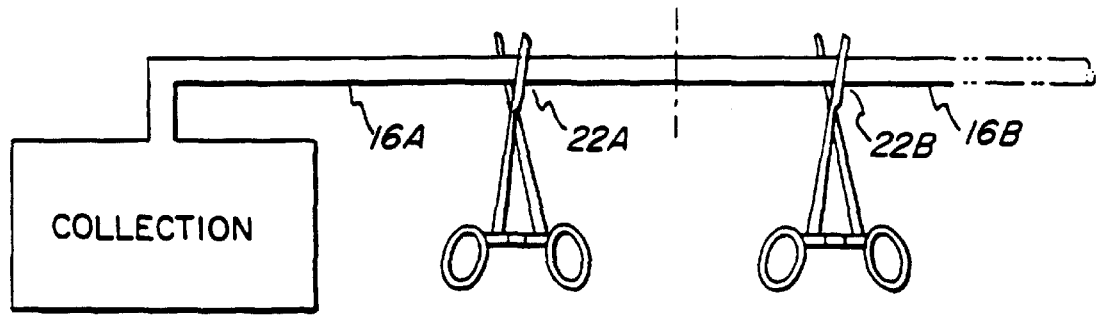
FIGS. 2A through 2E are planar illustrations of the sequential steps involved in making a sterile connection between two disassociated fluid conduit tube segments.
Figure 2B:
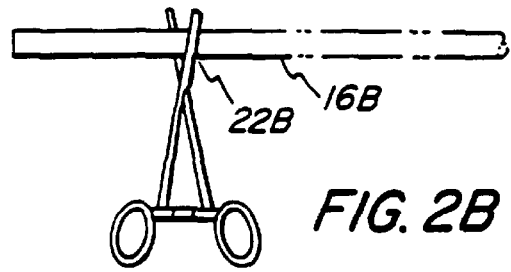

In a first step, at some appropriate point along the tubing 16 to which the collection container 18 is connected, hemostat clamps 22a and 22b are used to compress the silicone tubing at two spaced apart points so as to completely close off the central bore of the tubing, thus preventing any loss of sterility with respect to tubing and fluid on the opposite side of the clamps (i.e., to the left of clamp 22a and to the right of clamp 22b). Next, the tubing in the area between the clamps is cut, permitting the collection bag 18, its associated tubing 16a, and clamp 22a to be removed from the system for further processing, and leaving behind clamp 22b on the tubing 16b in connection with the active part of the culture system (FIG. 2B).

Figure 2C:
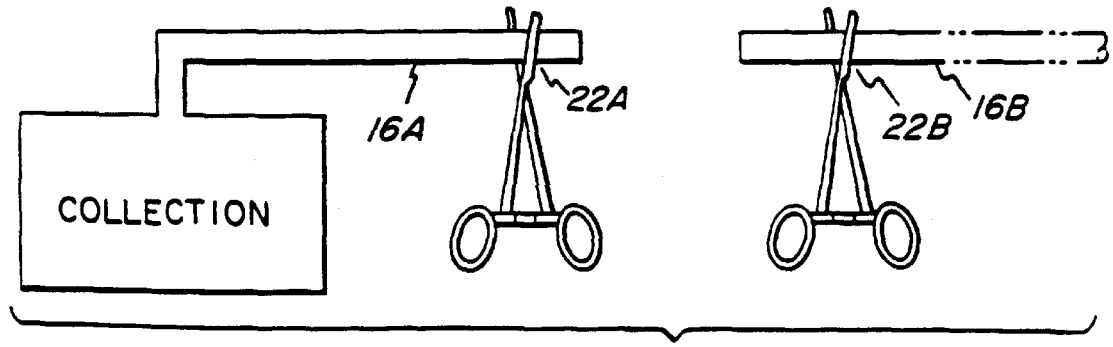
Figure 2D:
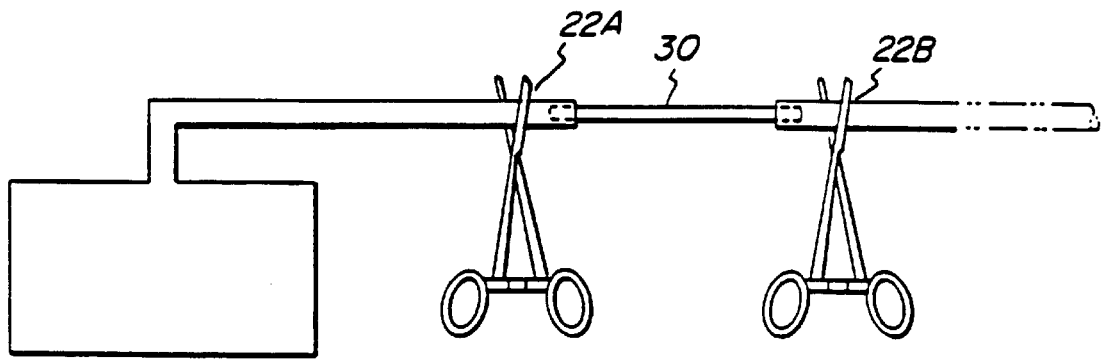
Figure 2E:
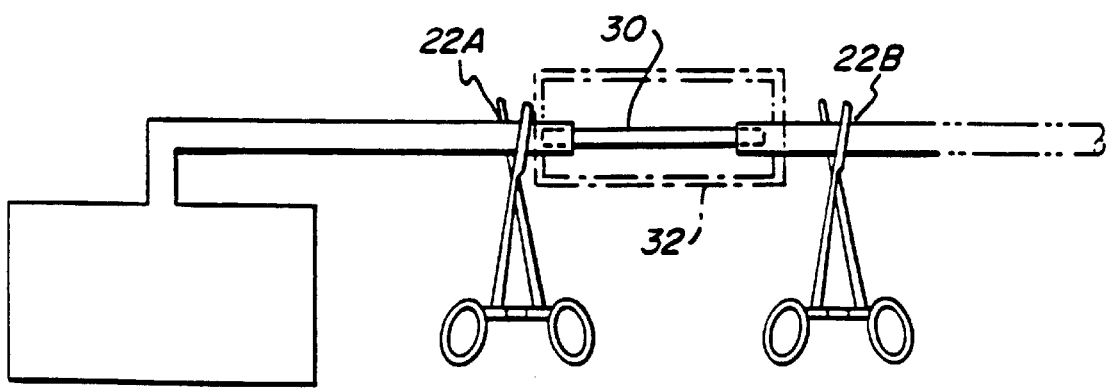

Next, a new collection container 18 and silicone tubing associated therewith is brought to proximity with the clamped tubing 16b. The new container and tubing will have been separately sterilized and clamped along its tubing length 16a with a clamp 22a so as to maintain the container and tubing behind (i.e., to the left of) the clamp in sterile condition (FIG. 2C).

In the next step of the sequence (FIG. 2D), the ends of a conductive hollow metal tube 30 are inserted, respectively, into the open bore of each of the tube portions on the "non-sterile" side of the hemostat clamps, thereby connecting the new collection container to the remainder of the culture system by way of the metal tube. The outer diameter of the metal tube 30 obviously is chosen so as to permit it to be inserted into the bore of each of the tubing segments, it generally being preferred, although not essential, that this sizing be such as to closely approximate the fluid conduit tube bore diameter to the point, say, of requiring a slight force-fitting of the metal tube within the bore, thereby providing a connection therebetween which is at least nominally fluid-tight and resistant to ingress of contaminants. The inner diameter of the metal tube is not of any critical importance so long as it is large enough to permit generally unrestricted fluid flow therein, yet not so large as to result in a metal tube wall which is so thin as to permit of breaking or deformation.

With the metal tube in place (FIG. 2E), at least a portion of the connected area between the clamps, including the metal tube 30, is subjected to induction heating to effect sterilization. This is accomplished by arranging the area to be treated in the field of a primary induction work coil 32 (e.g., copper). The work coil is connected to a source of alternating current (not shown). When activated, the alternating current supplied to the primary induction work coil induces a reverse alternating current in the portion of the conductive metal tube 30 lying within the magnetic field of the primary coil, producing heat in the metal tube.

In this manner, the metal tube 30 is heated to a temperature (generally, greater than about 400° F.) sufficient to kill contaminating bacteria and microorganisms on and within the metal tube, as well as within the bore of the silicone tubing surrounding the metal tube or in close proximity thereto. In this manner, then, the initially non-sterile connection established between the clamps is sterilized.

Following the sterilization procedure, it is possible to remove the hemostat clamps and thereby establish fluid communication between the collection container and the remainder of the system, now through the sterile connection comprised of the hollow metal tube 30, relying upon the force-fit between the metal tube and the silicone tubing bores to achieve a fluid-tight seal and to prevent ingress of contamination. In the preferred embodiment of the invention, however, and particularly needed when the outer diameter of the metal tube is not sufficient to provide a tight seal with the silicone tubing bore, the sterile connection is further enhanced by provision of means to compress the silicone tubing bore against the metal tube which it surrounds. These means may comprise the simple expedient of a knotted thread or more elaborate means such as mechanical clamping devices.

As will readily be appreciated, the foregoing method provides a way to effect sterile connections between tubing segments which is inexpensive, quick and easy to accomplish. Of particular note is the rapid heating afforded by induction heating, generally capable of bringing about the requisite heating in less than one minute. Still further, the induction heating method lends itself to employment with a current-generating unit and work coil which can be made essentially portable so that the sterile connections can be made at the site of the system (e.g., culture system, blood transfer station) rather than at some remote location where fixed sterilizing means are available. Obviously, of course, the materials needed to make the connections, i.e., simple hemostat clamps and metal tubing, are inexpensive and the operations easy to perform.

The method of the present invention is quite advantageous in yet other regards. By avoiding reliance upon complex connectors associated with tubing at predefined locations, the method of the present invention affords great flexibility in enabling one to invade a sterile fluid conduit system at any convenient location of choice thereon. Also, because the system does not rely upon thermoplastic tubing and the heating thereof to a point sufficient to achieve softening or melting, followed by cooling, to effect joinder of tube ends to each other or to an inserted connector element, the invention avoids concerns with degradation of tubing materials, requirements for excessive temperatures, and the like. Indeed, the induction heating to sterilization temperatures occurs within such a short period of time that little softening or melting, if any, of the tubing material occurs. This feature more readily permits re-use of the sterile connection point as a location for re-invasion of the sterile system and re-connection at that point using the present invention.

In the embodiment described above, it will be noted that, in the connection, metal tube 30 is shown as having a substantial portion not surrounded by silicone tubing, i.e., the respective ends of metal tube 30 are inserted into the respective bores of the silicone rubber tubing segments to be connected to a distance which results in bare metal being exposed at the connection. This feature is not strictly necessary inasmuch as the induction heating will effect heating of the metal tube even if the metal tube is completely within the silicone rubber tubing. Thus, the connection can be arranged such that the length of metal tube 30 and the lengths of the non-sterile portions of the silicone rubber tube segments are such as to end up with a connection wherein the rubber tube segments are pushed over the ends of the metal tube to the point where all of the metal tube is surrounded by the silicone rubber tube segments, and the ends of rubber tube segments abut. While making connections in this manner is not detrimental to operation of the invention, abutting of the rubber tube ends and complete enclosure of the metal tube are not required and it is obviously easier to make the connections such that only a portion of the metal tube ends need be fitted into the bores of the respective silicone rubber tube segments. The extent to which the metal tube ends are inserted into the silicone rubber tube segments is not critical per se, so long as it is a sufficient distance to achieve an integral connection and, if necessary, to permit the rubber tubing to be compressed about the metal tube ends with knotted threads or clamps after the sterile connection is made. In addition, the extent to which the metal tube 30 extends into the bore of each of the non-sterile silicone rubber tube segments generally should be such that it is at least far enough to permit the metal tube, when heated by induction, to conduct sufficient heat to the bores of the non-sterile tube segments adjacent thereto (i.e., not surrounding the metal tube) to effect sterilization thereof.

In a typical connection according to the invention, a twelve-gauge stainless steel tube three and one-half inches in length is employed. The silicone rubber tubing segments to be connected are clamped off so as to leave three-quarters of an inch of open (non-sterile) tubing after the clamping point for each segment. The stainless steel tube is then fitted into the bores of these respective open segments such that the metal tube ends terminate about one-sixteenth of an inch from the non-sterile side of the clamp point, thus leaving about 2.125 inches of exposed metal tubing in the connection. An induction heating unit is then moved into place, having a copper work coil sized so that at least a portion of the connection between the clamps can be arranged in the field of the work coil, taking care to keep the clamps themselves out of the field of the coil. Typically, the coil will be formed into a length which permits all of the exposed metal tube to lie within the coil field, and preferably is such that at least a portion of the metal tube surrounded by silicon rubber tubing at or near the ends of the metal tube also lies within the field of the work coil. The degree to which the connection lies within the field of the work coil is thus not critical per se, but need be at least sufficient such that induction heating of the metal tube will occur rapidly and uniformly, and that all initially non-sterile portions of the connector, including rubber tubing bores both including and not including the metal tube, can be sufficiently heated by conduction from the heated metal tube to effect sterilization of all such areas. For the dimensions set forth in this typical connection, the induction work coil preferably will be formed into a length of about three and one-half inches.

The induction heating to raise the temperature of the stainless steel tube to that sufficient to sterilize it and to permit it to conduct sufficient heat to non-sterile tubing bores adjacent the metal tube ends so as to also sterilize those areas, is effected using any suitable metal for the induction work coil and an operating frequency which will achieve the required induced current, and the consequent heating of the metal tube, in a relatively short time. Typically, the operating frequency will be in the radio frequency range, i.e., anywhere from between 10 kilocycles to 300,000 megacycles, but generally is in the range of from about 50 $KH_z$ to 1000 $KH_z$, and preferably from about 150 $KH_z$ to 700 $KH_z$. At such frequencies, stainless steel tubing can be heated to above about 400° F. generally in less than about one minute.

Figure 3:
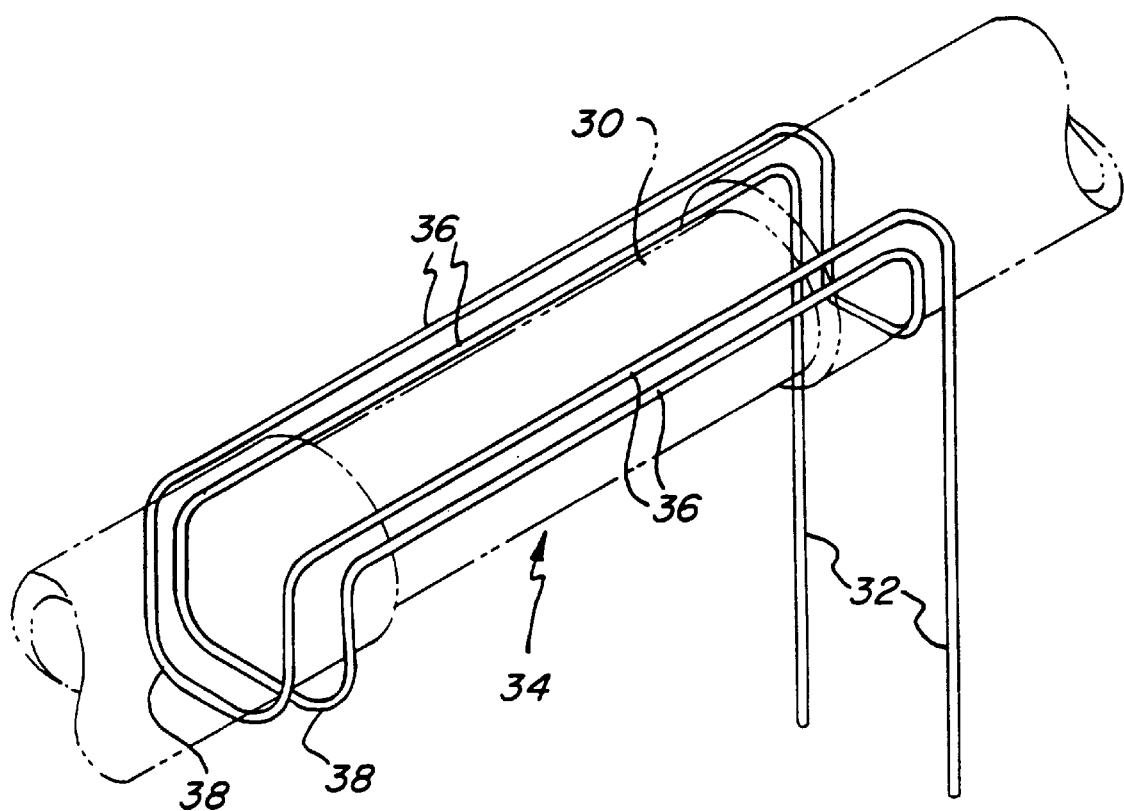
FIGS. 3 is a perspective view of an embodiment of a preferred primary induction work coil for use in the present invention.

A preferred configuration for the primary induction work coil for use in the invention is shown in FIG. 3. A continuous length of conductive metal coil material 32 is formed to provide an open channel 34 defined by opposed elongate lengths 36 of the metal coil and, below the plane thereof at respective ends of the channel, generally U-shaped lengths 38 of the metal coil. The dimensions of the elongate lengths 36 and U-shaped lengths 38 are chosen so that channel 34 is sized to accommodate the diameter of the thermostable tubing involved in the connection and such that a sufficient portion of conductive metal tube 30 (shown by the dotted lines within the channel) lies within the magnetic field brought about by application of alternating current to the primary work coil 32 to induce in the metal tube a reverse alternating current which causes the metal tube to heat up to sterilizing temperature. The ends of the length of coil material 32 are connected to a source of alternating current (not shown), preferably through flexible wiring of sufficient length to permit the work coil to be easily moved into a position to accommodate the connection area to be heated.

The primary induction work coil is preferably copper tubing (e.g., 3/16 inch) and, in the preferred embodiment, cooling water is flowed through the copper tubing. Other shapes into which the work coil can be formed are possible, so long as a suitable open channel is defined, into which the connection to be sterilized can be arranged so as to lie within the field of the current applied to the coil.

The present invention is applicable to the making of sterile connections between separate segments of fluid conduit tubing, wherein the fluid conduit tubing is generally a rubber-like hollow material of a degree of softness, flexibility and pliability to be useful as fluid tubing, to permit of compression to close off its hollow bore, and to permit of recovery to its original hollow configuration upon release of compressive force. The fluid conduit tubing must be made of thermostable material such that it does not decompose under the conditions of heating necessary to effect sterilization. As previously noted, it is not required, and is generally undesirable, to employ tubing materials which melt (and later resolidify) under the sterilizing temperature conditions employed, but the invention is at least generally applicable to utilization of such thermoplastic materials so long as they are thermostable. Greatly preferred for use in the invention is rubber tubing, particularly silicone rubber tubing.

The hollow conductive metal tube used for connecting the disassociated fluid conduit tube segments can be made of any conductive metal or conductive metal alloy which permits of induction heating without deformation to the extent needed to effect sterilization and which can conduct heat to adjacent or surrounding fluid conduit areas. Greatly preferred in this regard is stainless steel, although other metals or alloys obviously can be employed if desired.

The method and apparatus of the present invention may be employed to establish initial sterile interconnection between previously sterilized separate components of a system, as is the case in assembling an animal culture system with culture unit, oxygenation unit, collection container, media source, pumping mechanisms and associated tubing therebetween, or in assembling a blood transfer system or dialysis system or other like systems demanding sterile conditions.

The invention also is useful for invading an other wise sterile system to add or delete tubing or other components, this being accomplished by choosing a site along the fluid conduit tubing where the connection is to be made; isolating both sides of a tubing segment of predetermined length so as to maintain sterility in the segments outside the predetermined length; cutting the predetermined length of tubing so as to leave at least one isolated tubing segment having a free open end; bringing into general axial alignment with the free open end of the tube segment a second tube segment also having a free open end and isolated from a sterile environment on the other side of the point of isolation; joining the respective open ends by means of a hollow conductive metal tube arranged within the bore of each of the open ends; sterilizing the so-connected segments, and the tube therebetween, by means of induction heating; and there after removing the isolation means so as to establish fluid communication between sterile portions of the system, through the sterile connection.

Although the invention has been described with reference to particular embodiments, environments, materials and the like, it is to be understood that these are presented to illustrate and describe the fundamental features of the invention, and that many modifications are possible without departing from the spirit or scope of the invention as defined in the appended claims.

What is claimed is:

1. A method for invading a first sterile compressible rubber tubing segment, through the bore of which sterile fluid flows, so as to establish therewith sterile fluid flow with a second compressible rubber tubing segment, comprising the steps of:

(a) at two spaced-apart areas along the length of said first sterile tubing segment, compressing the tubing to an extent sufficient to close the tubing bore at each of said areas and thereby isolate the length of tubing between said areas;

(b) thereafter cutting said isolated length of tubing to provide a first tubing end segment;

(c) providing a second compressible rubber tubing segment having a second tubing end segment compressibly isolated from a sterile segment thereof;

(d) arranging within the bore of said first tubing end segment one of the respective two ends of a hollow conductive metal tube;

(e) arranging within the bore of said second tubing end segment the other end of said hollow conductive metal tube, thereby connecting said first sterile tubing segment and said second tubing segment;

(f) arranging at least a portion of said connected first and second tubing segments, including said hollow conductive metal tube, within the field of a primary induction work coil;

(g) supplying an alternating current to said work coil so as to cause said hollow conductive metal tube to be inductively heated to sterilize it and for sterilizing the bore portion of said first and second tubing end segments, thereby forming a sterile connection; and (h) thereafter removing the compression on the first sterile tubing segment and the second tubing segment so as to establish fluid communication therebetween through said sterile connection.

2. A method according to claim 1 wherein said first sterile compressible rubber tubing segment and said second compressible rubber tubing segment are composed of silicone rubber.

3. A method according to claim 1 further comprising the steps, after step (e), of applying a compressive element to said first tubing end segment to compress the bore of said first tubing end segment about the periphery of the end of the hollow conductive metal tube arranged within the bore of said first tubing end segment, and applying a compressive element to said second tubing end segment to compress the bore of said second tubing end segment about the periphery of the end of the hollow conductive metal tube arranged within the bore of said second tubing end segment.

* * * * *